(12) United States Patent
Chen

(10) Patent No.: US 6,388,441 B1
(45) Date of Patent: May 14, 2002

(54) METHOD FOR PROCESSING NMR DATA WITHOUT PHASE-ALTERNATING-PAIR (PAP) AVERAGING

(75) Inventor: Songhua Chen, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/691,514

(22) Filed: Oct. 18, 2000

(51) Int. Cl.[7] .................................................. G01R 3/00
(52) U.S. Cl. ........................................ 324/303; 324/300
(58) Field of Search ................................. 324/303, 300, 324/307, 309, 322

(56) References Cited

U.S. PATENT DOCUMENTS

| | | | |
|---|---|---|---|
| 5,291,137 A | 3/1994 | Freedman | 324/303 |
| 5,712,566 A | 1/1998 | Taicher et al. | 324/303 |
| 6,121,774 A | 9/2000 | Sun et al. | 324/303 |

FOREIGN PATENT DOCUMENTS

| | | |
|---|---|---|
| EP | 0967490 A2 | 12/1999 |
| WO | WO98/43064 | 10/1998 |

*Primary Examiner*—Hezron Williams
*Assistant Examiner*—Brij B. Shrivastav
(74) *Attorney, Agent, or Firm*—Madan, Mossman & Sriram, P.C.

(57) ABSTRACT

NMR data are acquired using a phase-alternation of the tipping pulse. Differences between consecutive samples acquired with same or different frequencies are determined and an average value of the differences is determined over a sample window and over a range of echoes. This average value, determined separately for the in-phase and quadrature component data is a measure of the systematic noise and may be applied to the in-phase and quadrature component data to give corrected data with a higher resolution than prior art methods of processing phase alternated pulse sequence data. The method may also be used to improve the resolution of multifrequency NMR data acquired with a gradient logging tool.

15 Claims, 4 Drawing Sheets

METHOD FOR PROCESSING NMR DATA WITHOUT PHASE-ALTERNATING-PAIR (PAP) AVERAGING

BACKGROUND OF THE INVENTION

1. Field of the Invention

The present invention relates generally to a method for measuring nuclear magnetic resonance properties of an earth formation traversed by a borehole, and more particularly, to a method for eliminating any ringing, such as magnetoacoustic ringing, and DC offset, during a nuclear magnetic resonance measurement.

2. Background of the Art

A variety of techniques are utilized in determining the presence and estimation of quantities of hydrocarbons (oil and gas) in earth formations. These methods are designed to determine formation parameters, including among other things, the resistivity, porosity and permeability of the rock formation surrounding the wellbore drilled for recovering the hydrocarbons. Typically, the tools designed to provide the desired information are used to log the wellbore. Much of the logging is done after the well bores have been drilled. More recently, wellbores have been logged while drilling, which is referred to as measurement-while-drilling (MWD) or logging-while-drilling (LWD).

One recently evolving technique involves utilizing Nuclear Magnetic Resonance (NMR) logging tools and methods for determining, among other things, porosity, hydrocarbon saturation and permeability of the rock formations. The NMR logging tools are utilized to excite the nuclei of the liquids in the geological formations surrounding the wellbore so that certain parameters such as spin density, longitudinal relaxation time (generally referred to in the art as $T_1$) and transverse relaxation time (generally referred to as $T_2$) of the geological formations can be measured. From such measurements, porosity, permeability and hydrocarbon saturation are determined, which provides valuable information about the make-up of the geological formations and the amount of extractable hydrocarbons.

The NMR instrument also typically includes an antenna, positioned near the magnet and shaped so that a pulse of radio frequency (RF) power conducted through the antenna induces an RF magnetic field in the earth formation. The RF magnetic field is generally orthogonal to the field applied by the magnet. This RF pulse, typically called a 90 degree pulse, has a duration and amplitude predetermined so that the spin axes of the hydrogen nuclei generally align themselves perpendicularly both to the orthogonal magnetic field induced by the RF pulse and to the magnetic field applied by the magnet. After the 90 degree pulse ends, the nuclear magnetic moments of the hydrogen nuclei gradually "relax" or return to their original alignment with the magnet's field. The amount of time taken for this relaxation, referred to as $T_1$, is related to petrophysical properties of interest of the earth formation.

After the 90 degree pulse ends, the antenna is typically electrically connected to a receiver, which detects and measures voltages induced in the antenna by precessional rotation of the spin axes of the hydrogen nuclei. The precessional rotation generates RF energy at a frequency proportional to the strength of the magnetic field applied by the magnet, this frequency being referred to as the Larmor frequency. The constant of proportionality for the Larmor frequency is known as the gyromagnetic ratio $\gamma_0$. The gyromagnetic ratio is unique for each different chemical elemental isotope. The spin axes of the hydrogen nuclei gradually "dephase" because of inhomogeneities in the magnet's field and because of differences in the chemical and magnetic environment within the earth formation. Dephasing results in a rapid decrease in the magnitude of the voltages induced in the antenna. The rapid decrease in the induced voltage is referred to as the free induction decay (FID). The rate of FID is typically referred to by the notation $T_2^*$. The FID decay rate consists of a first component referred to as "true $T_2$", which is due to internal nuclear environmental effects, and a second component resulting from microscopic differences in magnetic field and inhomogeneities in the earth formation. The effects of the second component can be substantially removed by a process referred to as spin-echo measurement.

One problem with analysis of NMR measurements is that the signal detected by the antenna includes a parasitic, spurious ringing that interferes with the measurement of spin-echoes. One source of the spurious signal is electromagnetic generation of ultrasonic standing waves in metal. The induced RF current within the skin depth of the metal interacts with the lattice in a static magnetic field through the Lorenz force and the coherent ultrasonic wave propagates into the metal to set up a standing wave. A reciprocal mechanism converts the acoustic energy, in the presence of the static field, to an oscillating magnetic field which is picked up by the antenna as a spurious, ringing signal.

Different types of magnetoacoustic interaction may produce a parasitic signal in the NMR antenna. Antenna wiring and other metal parts of the NMR logging tool can be affected by the static magnetic field and the RF field generated by the antenna. If the antenna is located within the strongest part of the magnet's field, when RF pulses are applied to the antenna, acoustic waves are generated in the antenna and the antenna sustains a series of damped mechanical oscillations in a process known to those skilled in the art as magnetoacoustic ringing. This ringing can induce large voltages in the antenna which are superimposed with the measurement of the voltages induced by the spin-echoes.

Another source of magnetoacoustic interaction is magnetorestrictive ringing which is typically caused when non-conductive magnetic materials, such as magnetic ferrite, are used in the antenna. If this magnetic material is located within the strong part of the RF field, application of RF pulses will generate acoustic waves in the magnet. The magnet will experience a series of damped mechanical oscillations upon cessation of the RF pulse. Magnetorestrictive ringing can also induce large voltages in the antenna which are superimposed with the measurement of the voltages induced by the spin-echoes.

One approach to reduce the effects of ringing has been to design the hardware to minimize the interaction between the electromagnetic fields and the materials in the device. For example U.S. Pat. No. 5,712,566 issued to Taicher et al. discloses a device in which the permanent magnet composed of a hard, ferrite magnet material that is formed into an annular cylinder having a circular hole parallel to the longitudinal axis of the apparatus. One or more receiver coils are arranged about the exterior surface of the magnet. An RF transmitting coil is located in the magnet hole where the static magnetic field is zero. The transmitting coil windings are formed around a soft ferrite rod. Thus, magnetoacoustic coil ringing is reduced by the configuration of the transmitting coil. Magnetorestrictive ringing of the magnet is reduced because the radial dependence of the RF field strength is relatively small due to use of the longitudinal dipole antenna with the ferrite rod. Further, magnetostrictive ringing is reduced because the receiver coil substantially removes coupling of the receiver coil with parasitic magnetic flux due to the inverse effect of magnetostriction.

Another commonly used approach to reduce the effect of ringing is to use a so-called phase-alternated-pulse sequence. Such a sequence is often implemented as $$RFA_{\pm x} - \tau - n \cdot (RFB_y - \tau - echo - \tau) - TW \quad (1)$$

where $RFA_{\pm x}$ is an A pulse, usually 90° tipping pulse and RFB is a pulse, usually a 180° refocusing pulse. The ± phase of RFA is applied alternately in order to identify and eliminate systematic noises, such as ringing and DC offset through subsequent processing. By subtracting the echoes in the − sequence from the pulses in the adjoining + sequence, the ringing due to the 180° is suppressed.

PCT publication WO 98/43064 of Prammer addresses the problem of ringing caused by the excitation pulse. A dual frequency acquisition is carried out with phase alternation, the separation between the two frequencies being one fourth of the reciprocal of the delay time in acquisition between the excitation pulse and the first refocusing pulse. Averaging of the two measurements then attenuates the effect of the ringing due to the excitation and refocusing pulses.

A drawback to the averaging of phase alternated data sequence is the requirement to combine two pulse sequence cycles. Measurements made by an NMR logging tool in this manner are therefore subjected to degradation in the vertical resolution due to the logging speed, wait time between each pulse sequence, and the data acquisition time. In addition, the logging tool moves along the longitudinal axis of the borehole between each of the measurements.

The problem with logging speed is exacerbated in multifrequency NMR measurements. A pulse sequence for an eight frequency logging operation may be denoted by $$CPMG(f_1, TE_1, RFA_+, n_1) - t_1 - CPMG(f_2, TE_2, RFA_+, n_1) - t_2 - \ldots$$

$$CPMG(f_8, TE_8, RFA_+, n_8) - t_8 - CPMG(f_1, TE_i, RFA_-, n_1) - t_1 - CPMG(f_2, TE_2, RFA_-, n_2) - t_2 \ldots CPMG(f_8, RFA_-, n_8) - t_8 \quad (2)$$

where $f_i$, $TE_i$ and $n_i$ are the frequency, interecho time and number of echoes for the i-th CPMG echo train. The CPMG pairs that only differ in the RFA phases are 8 sequences apart. Unless the logging speed is slowed down significantly, the two sensed volumes will be spatially separate and distinct the resolution of the tool is impaired.

The Sun patent teaches a method for suppressing ringing in which the acquired data consists of N normal echoes followed by M so-called "spoiled" echoes. The spoiled echoes do not have NMR signals from the formation and consist of noise only. By using the estimate of the noise signal, a signal may be recovered in which the noise has been attenuated. This method overcomes the disadvantages of PAP averaging discussed above; however, a substantial amount of time and energy is devoted to acquisition of spoiled echoes. As a result of this, either logging time has to be increased with an accompanying increase in the heating of the RF probe, which subsequently changes ringing, and increases power consumption duty cycle.

SUMMARY OF THE INVENTION

The present invention is a method of improving the resolution of NMR signals received from a formation surrounding a borehole. Any pulsed NMR tool in which a magnet arrangement is used to generate a static magnetic field having a substantially uniform field strength in a region of the formation surrounding the borehole, and in which an RF antenna is used to produce pulsed RF fields substantially orthogonal to the static field in the region of examination may be used. The tipping pulses in successive samples have alternating polarities. Differences between successive samples of the in-phase and quadrature component signals are determined and averaged over a sample window to give an estimate of the in-phase and quadrature component noise. These are indicative of the DC offset and the ringing noise in the received signals. The estimated in-phase and quadrature noise values are then used to correct the raw data. The sample window may be of fixed or variable length or may be recursive. In one embodiment of the invention, the noise estimate may be made variable to account for RF heating of the magnet and the antenna.

BRIEF DESCRIPTION OF THE DRAWINGS

For a detailed understanding of the present invention, references should be made to the following detailed description of the preferred embodiment, taken in conjunction with the accompanying drawings, in which like elements have been given like numerals, wherein.

DETAILED DESCRIPTION OF PREFERRED EMBODIMENTS

Figure 1:
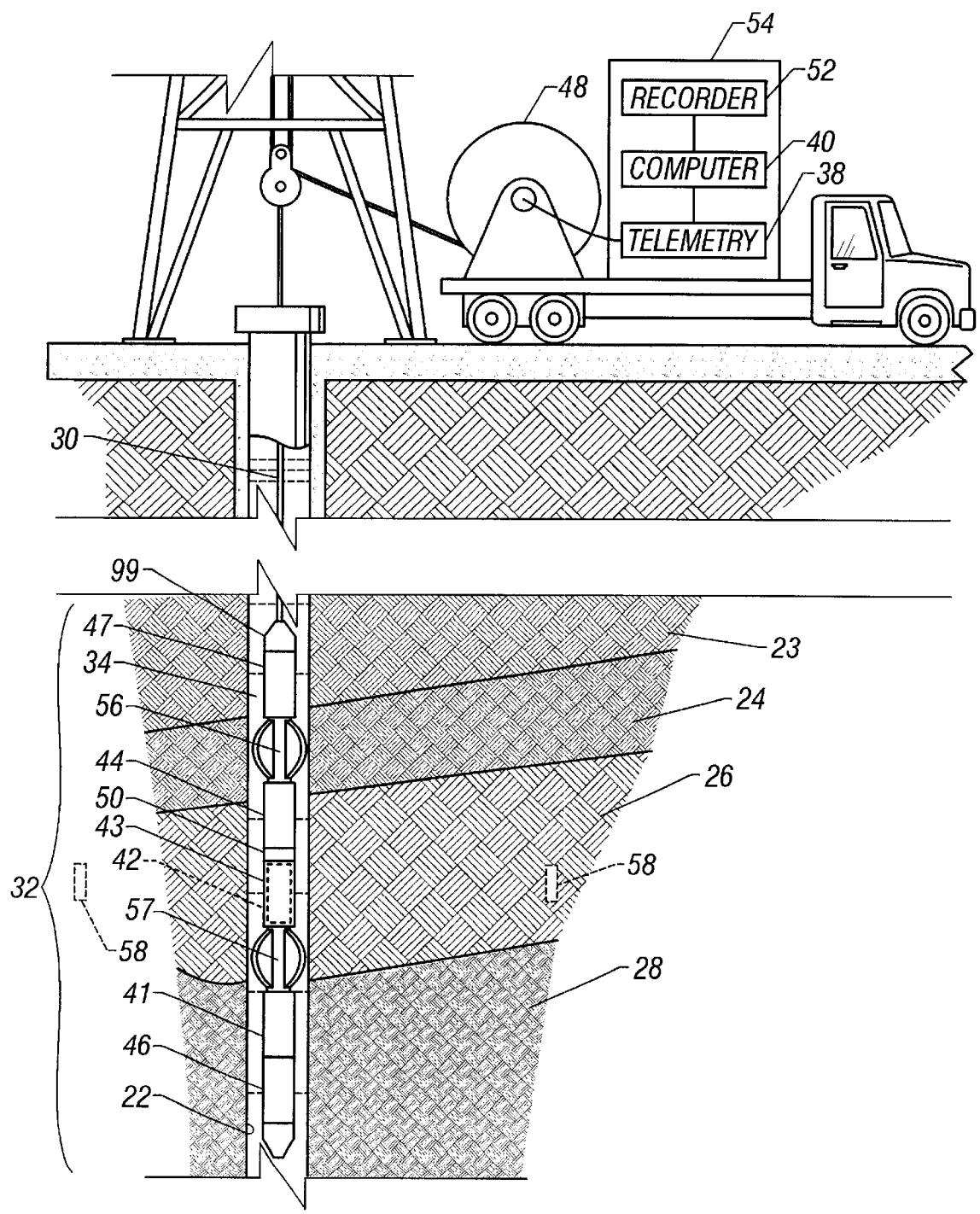
FIG. 1 (PRIOR ART) shows a nuclear magnetic resonance (NMR) well logging apparatus disposed in a wellbore penetrating earth formations.

FIG. 1 shows a well logging apparatus disposed in a wellbore 22 penetrating earth formations 23, 24, 26, 28 for making measurements of properties of the earth formations 23, 24, 26, 28. The wellbore 22 in FIG. 1 is typically filled with a fluid 34 known in the art as "drilling mud". A "sensitive volume", shown generally at 58 is disposed in one of the earth formations, shown at 26. The sensitive volume 58 is a predetermined portion of the earth formations 26 in which nuclear magnetic resonance (NMR) measurements are made, as will be further explained.

A string of logging tools 32, which can include an NMR apparatus according to the present invention, is typically lowered into the wellbore 22 by a means of an armored electrical cable 30. The cable 30 can be spooled and unspooled from a winch or drum 48. The tool string 32 can be electrically connected to surface equipment 54 by an insulated electrical conductor (not shown) forming part of the cable 30. The surface equipment 54 can include one part of a telemetry system 38 for communicating control signals and data to the tool string 32 and computer 40. The computer can also include a data recorder 52 for recording measurements made by the apparatus and transmitted to the surface equipment 54.

An NMR probe 42 according to the present invention can be included in the tool string 32. In the tool assembly shown in FIG. 1, the tool string 32 is centered within the wellbore 22 by means of a top centralizer 56 and a bottom centralizer 57 attached to the tool string 32 at axially spaced apart locations. The centralizers 56, 57 can be of types known in the art such as bowsprings. Other types of NMR logging tools are not designed for centralized operation and for such tools, a centralizer is not necessary.

Circuitry for operating the NMR probe 42 can be located within an NMR electronics cartridge 44. The circuitry can be connected to the NMR probe 42 through a connector 50. The NMR probe 42 is typically located within a protective housing 43 which is designed to exclude the drilling mud 34 from the interior of the probe 42.

Other well logging sensors (not shown separately for clarity of the illustration in FIG. 1) may form part of the tool string 32. As shown in FIG. 1, one additional logging sensor 47 may be located above the NMR electronics cartridge 44. Other logging sensors, such as shown at 41 and 46 may be located within or below the bottom centralizer 57. The other sensors 41, 46, 47 can be of types familiar to those skilled in the art and can include, but are not limited to, gamma ray detectors, formation bulk density sensors or neutron porosity detectors. Alternatively, parts of the NMR electronics may be located within electronic cartridges which form part of other logging sensors. The locations of the other sensors 41, 46, 47 shown in FIG. 1 are a matter of convenience for the system designer and are not to be construed as a limitation on the invention.

Those versed in the art would recognize that the NMR echo signals have two orthogonal components. For convenience, these are referred to hereafter as an in-phase and a quadrature component, even though in reality, delays in the electronic circuitry may produce a phase shift.. We denote these by $E_u$ and $E_v$. Denoting by j and k the sample and echo indices respectively, the data acquired in two consecutive acquisitions j and j+1 may be denoted by $$E_u(j,k) = E_{u0}(j,k) + \Psi_{u1}(j,k) \quad (3)$$

$$E_v(j,k) = E_{v0}(j,k) + \Psi_{v1}(j,k) \quad (4)$$

$$E_u(j+1,k) = E_{u0}(j+1,k) + \Psi_{u2}(j+1,k) \quad (5)$$

and $$E_v(j+1,k) = E_{v0}(j+1,k) + \Psi_{v2}(j+1,k) \quad (6)$$

where the subscripts 0 refer to system-noise-free signals but may include random noise and the ψ's are the system-noise contributions.

In prior art methods that use the PAP method, the systematic noise ψ is eliminated by averaging the odd and even samples, i.e., by averaging eqs. (3) and (5) for the in-phase component and by averaging eqs. (4) and (6) for the quadrature component. The polarity of the j+1 echo train has been flipped so that the summation is used instead of subtraction. This PAP approach is valid if $$\Psi_{u1}(j,k) = -\Psi_{u2}(j+1,k) \quad (7)$$

and $$\Psi_{v1}(j,k) = -\Psi_{v2}(j+1,k) \quad (8)$$

Eqs. (7) and (8) imply that the systematic noise is a slowly varying quantity. In the present invention, we utilized this slowly-varying characteristics of the systematic noise ψ. The average value of ψ is determined directly and removed from the raw data without the PAP averaging.

In a preferred embodiment of the present invention, instead of addition operations, subtractions are performed with eqs. (3)–(6). Thus, subtracting eq. (5) from eq. (3) gives $$\delta E_u(j,k) = \delta E_{u0}(j,k) + 2\Psi_{u1}(j,k) \quad (9)$$

while subtracting eq. (6) from eq. (4) gives $$\delta E_v(j,k) = \delta E_{v0}(j,k) + 2\Psi_{v1}(j,k) \quad (10)$$

Note that in the present method, the data are still acquired with alternating polarities; the difference from prior art methods lies in the way data from the plurality of depth samples are processed.

In a homogenous zone, and with a low-level random noise, $\delta E_{u0} \approx 0$ and $\delta E_{v0} \approx 0$. When this condition holds, eqs. (9) and (10) imply that the measured echo difference between two samples acquired with a 180° phase difference between the 90° RF tipping pulse provides a measure of the systematic noise. On the other hand, when the formation and the fluid change significantly between two neighboring levels, $\delta E_{u0}$ and $\delta E_{v0}$ cannot be ignored in eqs. (9) and (10). Furthermore, random noise is usually non-negligible. Thus, determination of ψ from eqs. (9) and (10) directly is often unsuccessful. Furthermore, the echo by echo estimate of system noise is unnecessary because the system noise are correlated. The present invention does not require this condition of homogeneity between successive samples and the random noise effect is eliminated.

The magnitude of the systematic noise (which includes ringing and DC offset) is not expected to change significantly from one depth to another based upon known electronics theory and NMR measurements. For small variations of temperature and formation properties, the variation of $\Psi_{1u}(j)$ and $\Psi_{1v}(j)$ with j is insignificant. In addition, as long as the temperature does not change appreciably during an NMR measurement, $\Psi_{1u}(j)$ and $\Psi_{1v}(j)$ are independent of the echo number k. Accordingly, the echo index k may be dropped from eqs. (9) and (10).

Figure 2A:
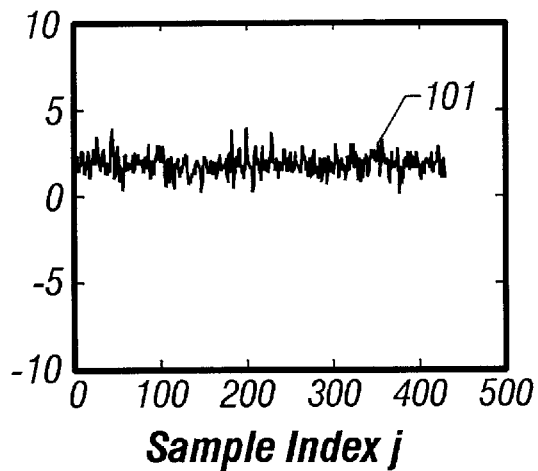
FIGS. 2A and 2B show examples of the magnitude and phase of the DC offset in an NMR survey.
Figure 2B:
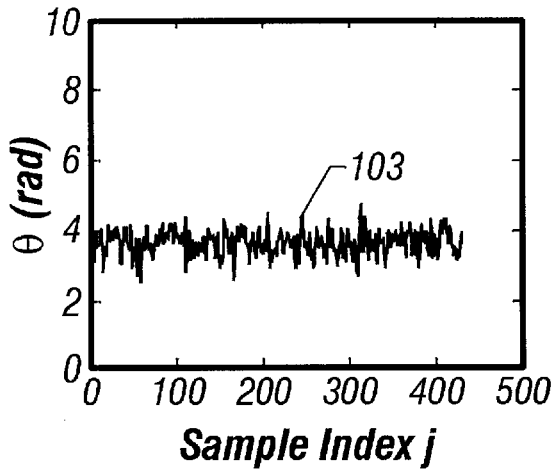
Figure 3A:
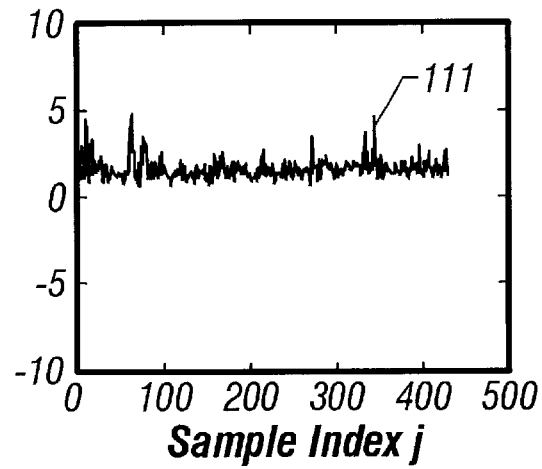
FIGS. 3A and 3B show examples of the magnitude and phase of the ringing noise in an NMR survey.
Figure 3B:
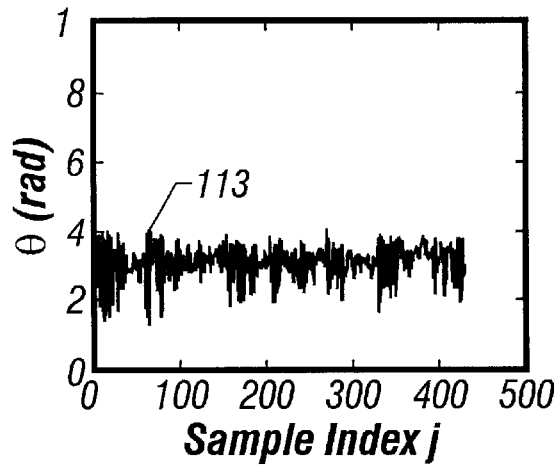

FIGS. 2a and 2b show an example of the magnitude 101 and the phase 103 of the DC offset of NMR signals for a plurality of values of the sample index j corresponding to different depths. Similarly FIGS. 3a and 3b show an example of the magnitude 111 and phase 113 of the random noise. The random noise and the systematic noise are comparable in magnitude and the desired NMR signal is buried within the random noise. However, there is little systematic variation in the amplitude and phase of both the DC offset and the random noise. Accordingly, the assumption made in the present invention that $\Psi_{1u}$ and $\Psi_{1v}$ do not vary significantly with the sample index is justified.

With these assumptions, the average values of $\Psi_{1u}$ and $\Psi_{1v}$ may be determined as $$\overline{\Psi}_{ul} = \frac{\sum_{j=J_1,2}^{J_2} \sum_{k=1}^{K} \delta E_u(j,k)}{2\left(\frac{J_2-J_1}{2}+1\right) \cdot K}$$

$$= \frac{\sum_{j=J_1,2}^{J_2} \sum_{k=1}^{K} \delta E_{u0}(j,k) + \sum_{j=J_1,2}^{J_2} \sum_{k=1}^{K} 2\Psi_{ul}(j,k)}{2\left(\frac{J_2-J_1}{2}+1\right) \cdot K} \quad (11)$$

-continued $$\approx \frac{\sum_{j=J_1}^{J_2}\sum_{k=1}^{K}\Psi_{ul}(j)}{\left(\frac{J_2-J_1}{2}+1\right)\cdot K}$$

where the index j is incremented in steps of 2, i.e., $j=J_1, J_1+2, J_1+4, \ldots J_2$.
and $$\Psi_{vl} = \frac{\sum_{j=J_1,2}^{J_2}\sum_{k=1}^{K}\delta E_v(j,k)}{2\left(\frac{J_2-J_1}{2}+1\right)\cdot K} \quad (12)$$

$$= \frac{\sum_{j=J_1,2}^{J_2}\sum_{k=1}^{K}\delta E_{vO}(j,k) + \sum_{j=J_1,2}^{J_2}\sum_{k=1}^{K}2\Psi_{vl}(j,k)}{2\left(\frac{J_2-J_1}{2}+1\right)\cdot K}$$

$$\approx \frac{\sum_{j=J_1,2}^{J_2}\sum_{k=1}^{K}\Psi_{vl}(j)}{\left(\frac{J_2-J_1}{2}+1\right)\cdot K}$$

The averaging is performed over a sample range from $J_1$ to $J_2$ where $J_2-J_1 \gg 1$. In different embodiments of the invention, the window defined by this sample range may be a window of fixed length, a window of variable length, or a recursive window (one with substantial overlap between windows).

These determined corrections are then applied to the raw data to give corrected measurements $E_u$ and $E_v$ as $$E_{uc}(j,k) = E_u(j,k) - \overline{\Psi}_{u1} \quad (13)$$

$$E_{uc}(j+1,k) = E_u(j+1,k) + \overline{\Psi}_{u1} \quad (14)$$

$$E_{vc}(j,k) = E_v(j,k) - \overline{\Psi}_{v1} \quad (15)$$

and $$E_{vc}(j+1,k) = E_v(j+1,k) + \overline{\Psi}_{v1} \quad (16)$$

Note that in eqs. (13) and (15) the mean value of the noise is subtracted whereas in eqs. (14) and (16), the mean value is added. This is consistent with the flipping of the polarities of the signals in eqs. (3) and (4).

Figure 4:
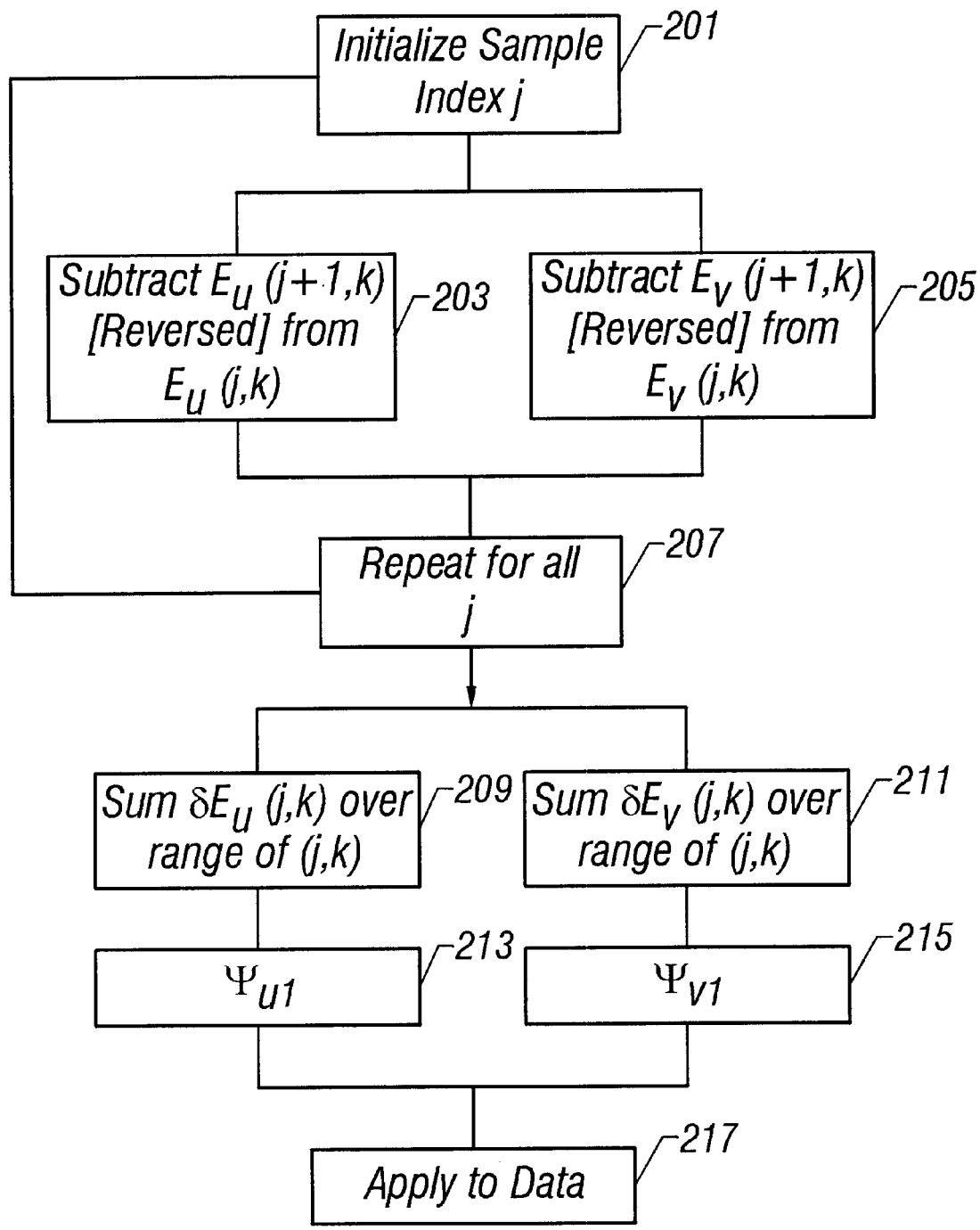
FIG. 4 shows a schematic flow chart of the method of the present invention.

FIG. 4 shows a schematic flow chart of the method of the present invention. Starting at 201, initial-phase and quadrature components are defined for two successive samples (with the polarity of the second sample reversed) and the second echo train is subtracted from the first echo train 203, 205 as given by eqs. (9) and (10). This is repeated for all samples of interest 207. The summation of these differences (and averaging) as given by eqs. (11) and (12) is performed at 209, 211 to give estimates of the noise $\Psi_{u1}$ and $\Psi_{v1}$ 213, 215. These noise estimates are then applied to the data 217 to give corrected in-phase and quadrature echo trains according to eqs. (13)–(16).

Figure 5:
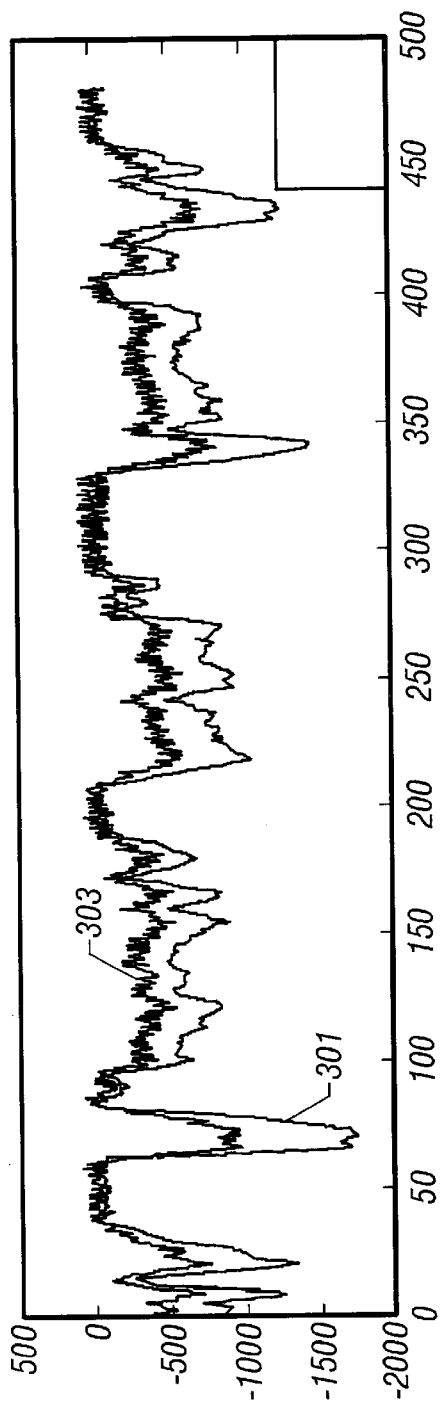
FIG. 5 is an example of the inline and quadrature component data acquired in a NMR survey.

Turning now to FIG. 5, an example of the inline 301 and quadrature 303 component data acquired in a NMR survey (a total of 480 samples) are shown. Note the vertical axis represents sum of echoes (summation over index k) for each sample.

Figure 6:
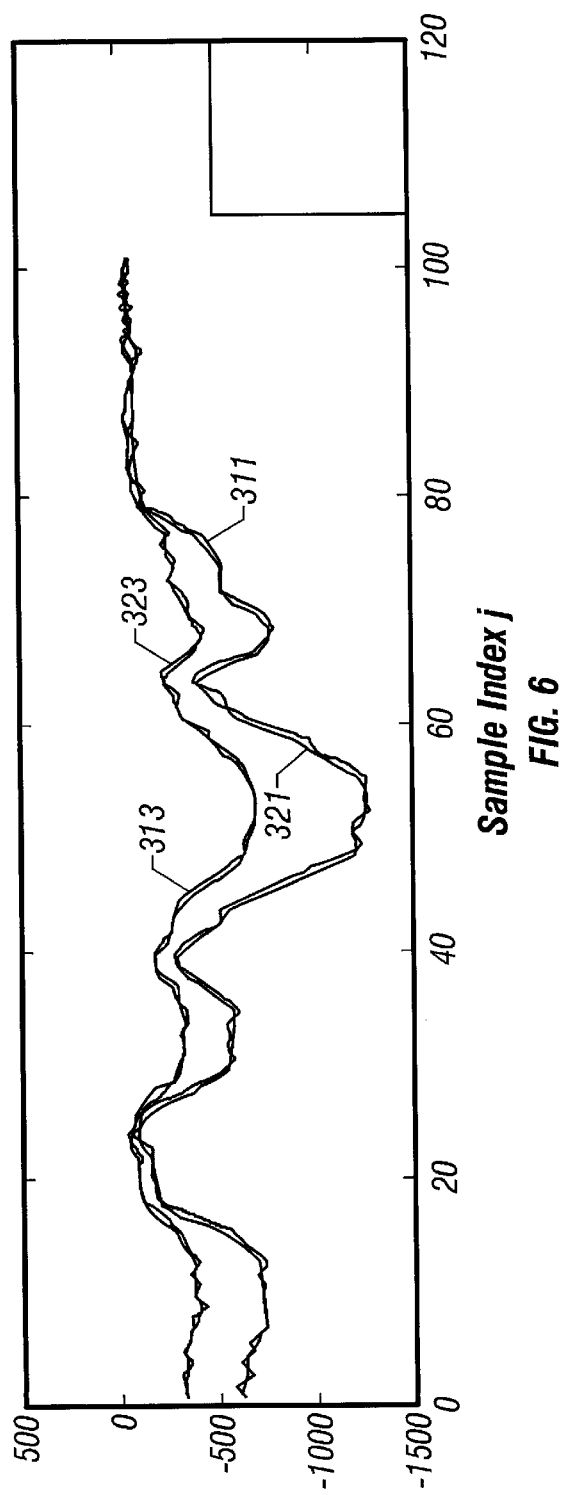
FIG. 6 shows the results of applying the method of the present invention to a portion of the data of FIG. 5 and a comparison with results from the prior art PAP method.

FIG. 6 shows the results of applying the method of the present invention to a portion of the data of FIG. 5 for samples 1–120. Shown are the corrected in-phase 311 and quadrature 313 component data. Also shown for purposes of comparison are the results of prior art PAP data acquisition and processing with the in-phase 321 and quadrature 323 component. The results of using the method of the present invention are comparable to those of the PAP method. It does appear that the present method gives results with improved resolution when compared to the PAP method: curves 311 and 313 show more fine scale detail than do curves 321 and 323. The example is for a dual frequency data acquired with slow logging speed. Should more frequency and high logging speed are used, the improvement of resolution with the present art would be more obvious.

The method of the present invention is particularly useful when used in a so-called gradient tool wherein the static magnetic field has a gradient and successive samples are acquired with different RF frequencies. In such an acquisition method, the RF frequency is changed between successive samples. Each of the frequencies excites signals from a different region of the formation, i.e., one where the Larmor frequency corresponding to the static field strength matches the frequency of the RF pulse. In such a case, with the prior art PAP method, the number of samples between the occurrence of the same frequency with the alternate phase increases multiplicatively by the number of frequencies used, so that the loss of resolution is even greater. Application of the method of the present invention then involves separating out the data sequences corresponding to each frequency and processing the data for each frequency separately according to the method described above.

When the CPMG sequence comprises a short interecho spacing with a large number of echoes, those versed in the art would recognize that the heating produced by the RF pulses would produce an increase in temperature and consequently the ringing noise may be changed. In an optional embodiment of the invention, correction is made for this by introducing a linear term to the noise level. This may be done by suitable weights in eqs. (11) and (12).

While the foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A method for determining a parameter of interest of a volume of earth formation with a borehole tool conveyed in a borehole within the formation, the method comprising:
   (a) using a magnet assembly on the borehole tool for producing a static magnetic field having in said volume of the formation and aligning nuclear spins within said volume parallel to a direction of the static field;
   (b) producing a radio frequency (RF) magnetic field in said volume of the formation, said RF magnetic field having a first frequency and a direction substantially orthogonal to a direction of the static field, the RF field including a pulse sequence:

$$T-\tau-(R-\tau\text{echo}-\tau)_k-TW$$

wherein T is a tipping pulse for tipping the nuclear spins at an angle substantially equal to ninety degrees to cause precession thereof, TW is a waiting time, $\tau$ is the Carr-Purcell time, R is a refocusing pulse and $k=1, 2, \ldots K$, is the echo index, where k is the number of echoes collected in a single sequence of pulses; and $(R-\tau-\text{echo}-\tau)_k$ represents the time sequence from echo #1 to echo #K;

(c) measuring with a receiver coil on the borehole tool in-phase and quadrature components of signals including a desired signal indicative of the response of the formation to the pulsed RF field, said measured in-phase and quadrature signals further including an additive systematic noise;

(d) repeating steps (b) and (c) defining a plurality of samples at a plurality of depths in the borehole wherein a polarity of the tipping pulse is reversed between successive samples; and (e) processing said measured signals at the plurality of depths to determine a level of said additive systematic noise in said in-phase and quadrature component signals.

2. The method of claim 1 wherein the additive systematic noise in the in-phase signal is different from the additive systematic noise in the quadrature signal.

3. The method of claim 1 wherein the additive systematic noise includes at least one of (i) a DC offset to the signal (ii) a ringing noise produced by ringing of the magnet assembly induced by the RF magnetic field, and, (iii) a ringing noise produced by ringing of said receiver coil.

4. The method of claim 1 wherein prior to step (d), steps (b) and (c) are repeated with the RF magnetic field having a second frequency different from the first frequency.

5. The method of claim 4 wherein processing said measured signals further comprises separately processing the signals corresponding to the first frequency and the second frequency to determine a level of the additive noise in the in-phase and quadrature component signals at each of said frequencies.

6. The method of claim 1 wherein processing said measured signals further comprises summing the in-phase and quadrature signals over a plurality of values of k, giving summed in-phase and quadrature signals.

7. The method of claim 6 wherein processing said measured signals further comprises determining a difference between a summed in-phase signal for a selected sample and a summed in-phase signal for a consecutive sample.

8. The method of claim 6 wherein processing said measured signals further comprises determining a difference between a summed quadrature signal for a selected sample and a summed quadrature signal for a consecutive sample.

9. The method of claim 7 wherein processing said measured signals further comprises determining said difference for a plurality of selected samples over a sample window to give a plurality of differences.

10. The method of claim 8 wherein processing said measured signals further comprises determining said difference for a plurality of selected samples over a sample window to give a plurality of differences.

11. The method of claim 9 wherein processing said measured signals further comprises summing said plurality of differences.

12. The method of claim 10 wherein processing said measured signals further comprises summing said plurality of differences.

13. The method of claim 11 wherein processing said measured signals further comprises forming a weighted sum of said plurality of differences.

14. The method of claim 12 wherein processing said measured signals further comprises forming a weighted sum of said plurality of differences.

15. The method of claim 1 further comprising applying a correction based upon said additive noise in the in-line and quadrature components to the measured in-phase and quadrature signals.

\* \* \* \* \*